(12) United States Patent
Martinez Gil et al.

(10) Patent No.: US 11,446,304 B2
(45) Date of Patent: Sep. 20, 2022

(54) CDC-7-INHIBITOR COMPOUNDS AND USE THEREOF FOR THE TREATMENT OF NEUROLOGICAL CONDITIONS

(71) Applicant: CONSEJO SUPERIOR DE INVESTIGACIONES CIENTIFICAS (CSIC), Madrid (ES)

(72) Inventors: Ana Martinez Gil, Madrid (ES); Daniel I. Perez, Madrid (ES); Carmen Gil Ayuso-Gontán, Madrid (ES); Angeles Martin-Requero, Madrid (ES); Elisa Rojas Prats, Madrid (ES); Loreto Martinez-Gonzalez, Madrid (ES); Concepción Perez, Madrid (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 151 days.

(21) Appl. No.: 16/495,613

(22) PCT Filed: Mar. 21, 2018

(86) PCT No.: PCT/ES2018/070215
§ 371 (c)(1),
(2) Date: Dec. 2, 2019

(87) PCT Pub. No.: WO2018/172587
PCT Pub. Date: Sep. 27, 2018

(65) Prior Publication Data
US 2020/0093828 A1 Mar. 26, 2020

(30) Foreign Application Priority Data
Mar. 22, 2017 (ES) .................. P201730399

(51) Int. Cl.
*A61K 31/52* (2006.01)
*A61P 25/28* (2006.01)

(52) U.S. Cl.
CPC .............. *A61K 31/52* (2013.01); *A61P 25/28* (2018.01)

(58) Field of Classification Search
CPC .................................................. A61K 31/52
See application file for complete search history.

(56) References Cited

U.S. PATENT DOCUMENTS

| 3,232,937 A | 1/1966 | Hitchings et al. |
| 2011/0015172 A1 | 1/2011 | Penning et al. |
| 2013/0072506 A1 | 3/2013 | Zahajska et al. |

FOREIGN PATENT DOCUMENTS

| EP | 1444982 A1 * | 2/2003 | ........... A61K 31/519 |
| EP | 1352910 | * 10/2003 | |
| EP | 1352910 W1 | 10/2003 | |
| EP | 1444982 | 8/2004 | |
| JP | 2004/161716 | * 6/2004 | |
| JP | 2004161716 A | 6/2004 | |
| WO | 1997018212 A1 | 5/1997 | |
| WO | 2007124288 | 1/2007 | |
| WO | 2010065923 A2 | 6/2010 | |

OTHER PUBLICATIONS

Wagner et al., Pharmazie (1974), 29(3), 160-4.*
Lewis et al., Journal of Medicinal & Pharmaceutical Chemistry (1962), 5, 607-17.*
Nicole F. Liachko, "CDC7 inhibition blocks pathological TDP-43 phosphorylation and neurogegeneration", Manuscript, Jul. 2013, 39-52, vol. 74, No. 1, Annals of Neurology 2013.
Sukriti Nag, "TDP-43 pathology and memory impairment in elders without pathologic diagnoses of AD of FTLD", Abstract, 653-661, 2017 American Academy of Neurology.
Robert S. Wilson, "TDP-43 Pathology, Cognitive Decline, and Dementia in Old Age", Article, Nov. 2013, 1418-1424, vol. 70 No. 11, JAMA Neurology.
Yunsong Tong, "Azaindole-Based Inhibitors of Cdc7 Kinase: Impact of the Pre-DFG Residue, Val 195", Letter, 2013, 211-215, ACS Medical Chemistry Letters.
Christoph Kamper, "Sustainable synthesis and automated deposition: an accessible discovery screening library of fragment-like purines", Paper, 2012, 541-542, Mol Divers 16, Springer.
Li Di, "High throughout artificial membrane permeability assay for blood-brain barrier", Journal, 2003, 223-232, Science Direct, European Journal of Medical Chemistry.
Sarah M. Trattnig, "Discovery of a Novel Allosteric Modulator of 5-HT3 Receptors-Inhibition and potentiation of cys-loop receptor signaling through a conserved transmembrane intersubunit site", Journal, 2012, 25241-25253, vol. 287 No. 30, ASBMB Journal of Biological Chemistry.
H.E. Skipper, "Structure-Activity Relationships and Cross-Resistance Observed on Evaluation of a series of Purine Analogs against Experimental Neoplasms", Journal, 1959, 425-437, American Association for Cancer Research.
Leland R. Lewis, "The Preparation and Antitumor Activity of Certain Derivatives of 6-Mercaptopurine", 1962, 607-617, Journal, Arizona State University.
Naturstofhe, Abstract, 9, 1978, Chemischer Informationsdienst, No. 22.
Francois Denizot, "Rapid colorimetric assay for cell growth and survival—Modifications to the tetrazolium dye procedure giving improved sensitivity and reliability" Journal, 1986, 271-277, vol. 89, Journal of Immunological Methods.
Ashish K. Pathak, "Antimycobacterial Agents. 1. Thio Analogues of Purine", Article, 2004, 273-276, vol. 47, Journal at Medicinal Chemistry.

(Continued)

*Primary Examiner* — Paul V Ward
(74) *Attorney, Agent, or Firm* — Hayes Soloway P.C.

(57) ABSTRACT

The present invention relates to a series of substituted purine derivatives capable of inhibiting CDC7 kinase activity and, as such, suitable for use in the treatment of neurological diseases such as, inter alia, Alzheimer's disease, amyotrophic lateral sclerosis or frontotemporal dementia, involving hyperphosphorylation of TDP-43 and the subsequent formation of aggregates, induced by CDC7.

9 Claims, 2 Drawing Sheets

(56) References Cited

OTHER PUBLICATIONS

Reynier A. Tromp, "Inhibition of Nucleoside TRansport by New Analogues of 4Nitrobenzylthioinosine: Replacement of the Ribose Moiety by Substituted Benzyl Groups", Journal, 2004, 5441-5450, vol. 47, Journal of Medicinal Chemistry.

Martin J. Wanner, "Synthesis and Antitumor Activity of Methyltriazene Prodrugs Simultaneously Releasing DNA-Methylating Agents and the Antiresistance Drug O6- Benzylguanine", Journal, 2004, 6875-6883, vol. 47, Journal of Medicinal Chemistry.

Grant L. Iverson, "A critical review of chronic traumatic encephalopathy", Article, 2015, 276-293, vol. 56, Neuroscience and Biobehavioral Reviews.

Laurent F. Bonnac, "Structure activity relationship, 6-modified purine riboside analogues to activate hSTING, stimulator of interferon genes", Journal, 2019, 1-5, Bioorganic & Medicinal Chemistry Letters.

European Search Report of EP Application No. 18771997.6 (corresponding to PCT/ES2018/070215), dated Aug. 4, 2020.

Trattning, S.M. et al. "Discovery of a Novel Allosteric Modulator of 5-HT3 Receptors: Inhibition and Potentiation of Cys-Loop Receptor Signaling through a Conserved Transmembrane Intersubunit Site" The Journal of Biological Chemistry, vol. 287, No. 30 (2012), pp. 25241-25254.

Wagner G. et al. "Immunosuppressive Antigen Conjugate. Part 19. Synthesis of 6 Mercaptopurine Protein Conugates by Means of Imido Ester Coupling" Pharmazie, (1977), vol. 32, No. 12, pp. 748-750.

Ma, Y. et al. "Synthesis, Anti-cancer Activity and Mechanism Study of 6 Mercapto-Purine Derivatives" Letters in Drug Design & Discovery, 2016, 13(6), pp. 570-576.

Kamper, C. et al. "Sustanable Synthesis and Automated Deposition: an Accessible Discovery Screening Library of Fragment-like Purines" Molecular Diversity, 2012, 16(3), pp. 541-551.

CAS Registry No. 908079-14-1; STN Entry Date Sep. 21, 2006.
CAS Registry No. 93353-63-0, STN Entry Date Dec. 18, 1984.
CAS Registry No. 1112281-40-9; STN Entry Date Feb. 26, 2009.
AU Examination Report 1 dated May 14, 2021.
AU Examination Report 2 dated Feb. 10, 2022.
AU Examination Report 3 dated Mar. 30, 2022.

* cited by examiner

CDC-7-INHIBITOR COMPOUNDS AND USE THEREOF FOR THE TREATMENT OF NEUROLOGICAL CONDITIONS

CROSS-REFERENCE TO RELATED APPLICATIONS AND PRIORITY

This patent application claims priority from PCT/ES2018/070215 filed Mar. 21, 2018, which claims priority from ES P201730399 filed Mar. 22, 2017. Each of these patent applications are herein incorporated by reference in their entirety.

The present invention refers to a series of substituted purine derivatives that are capable of inhibiting the activity of CDC7 kinase, making them useful for the treatment and/or prevention of neurological diseases such as amyotrophic lateral sclerosis, Alzheimer's disease or frontotemporal dementia, where hyperphosphorylation of TDP-43 and subsequent formation of aggregates induced by CDC7 are produced.

STATE OF THE ART

Hyperactivity of kinases occurs in many types of diseases and particularly in neurodegenerative diseases and cancer. Hyperphosphorylation of the TDP-43 protein induces the formation of aggregates that have been detected in patients with amyotrophic lateral sclerosis or frontotemporal lobular degeneration. It has been detected that CDC7 kinase is responsible for the dual hyperphosphorylation of TDP-43 in serines 409/410 in certain models, so the inhibition of CDC7 would be an interesting strategy to develop drugs for neurodegenerative diseases, such as amyotrophic lateral sclerosis (ALS) or frontotemporal lobular degeneration (Lianchko, N. F. et al.), *Ann Neurol.* 2013 74(1): 39-52). There are other neurological diseases also mediated by TDP-43, such as chronic traumatic encephalopathy and age-associated cognitive impairment (Iverson G L, et al., *Neurosci Biobehav Rev.* 2015 September; 56: 276-293; Nag S, et al., *Neurology.* 2017 Feb. 14; 88(7): 653-660; Wilson R S, et al., *JAMA Neurol.* 2013 November; 70(11): 1418-1424).

Document US2013/0072506A1 describes 6,8-substituted purine derivatives that are useful for a number of therapeutic and cosmetic uses. Among the possible therapeutic uses, mention is made of the treatment of multiple sclerosis or as anti-neurodegenerative drugs.

Document WO2007/124288A1 describes a series of compounds with an indazole structural nucleus that have the ability to inhibit CDC-7 and that are useful for the treatment of a disease in which this kinase is involved, such as cancer.

In *ACS Med. Chem. Lett.* 2013, 4, 211-215, Penning et al. describe a study on the interaction of azaindole-derived compounds with the CDC-7 and the possibility of using these compounds in cancer therapy.

Document US2011/015172A1 describes a family of pyrolpyrazines that are kinase-inhibitors such as CDC-7 and their use for the treatment of kinase-associated diseases such as cancer.

DESCRIPTION OF THE INVENTION

The present invention provides a series of purine-derived compounds that are inhibitors of CDC-7 and useful as potential drugs for diseases mediated by TDP-43 proteinopathies, such as Alzheimer's disease, amyotrophic lateral sclerosis (ALS) and frontotemporal dementia.

Therefore, in a first aspect, the present invention refers to the use of a compound formula (I)

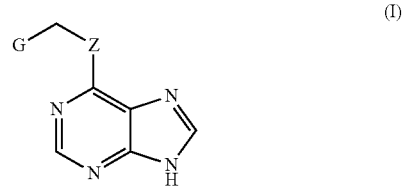

wherein:
G represents a group selected from aryl, heteroaryl or $C_1$-$C_{10}$ alkyl, any of which is optionally substituted by at least one substituent selected from $CF_3$, $C_1$-$C_6$ alkyl, S—$C_1$-$C_6$ alkyl, halogen, CN, O—$C_1$-$C_6$ Alkyl, $NO_2$, COO—$C_1$-$C_6$ Alkyl, NHCO—$C_1$-$C_6$ Alkyl, $NH_2$ and NH—$C_1$-$C_6$ alkyl, or optionally substituted by two substituents forming a cycle condensed to group G when it is an aryl or a heteroaryl and Z is selected from O or S;
or any of its pharmaceutically acceptable salts, solvents or isomers for the manufacture of a medicament for the treatment and/or prevention of pathologies related to the TDP-43 protein, in particular with post-translational modifications of TDP-43. These compounds are inhibitors of CDC7 in the phosphorylation of TDP-43.

In a preferred performance G is an aryl group optionally substituted by at least one substituent selected from $CF_3$, $C_1$-$C_{6b}$alkyl, S—$C_1$-$C_6$ alkyl, halogen, CN, O—$C_1$-$C_6$ alkyl, $NO_2$, COO—$C_1$-$C_6$ alkyl, NHCO—$C_1$-$C_6$ alkyl, $NH_2$ and NH—$C_1$-$C_6$ alkyl, or optionally substituted by two substituents forming a cycle condensed to the aryl group, more preferably the aryl group is a phenyl that can optionally be substituted and the compound formula (I) would be the compound formula (II):

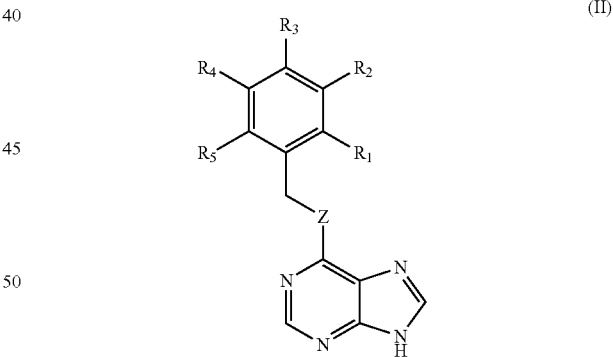

wherein:
$R_1$ to $R_5$ are each independently selected from H, $CF_3$, S—$C_1$-$C_6$ Alkyl, halogen, $C_1$-$C_6$ Alkyl, CN, O—$C_1$-$C_6$ Alkyl, $NO_2$, COO—$C_1$-$C_6$ Alkyl, NHCO—$C_1$-$C_6$ alkyl, $NH_2$ and NH—$C_1$-$C_6$ Alkyl or two of the radicals $R_1$ to $R_5$ form a phenyl-condensed cycle; and
Z is selected from O or S.

The term "aryl", in the present invention, refers to single or multiple aromatic rings, which have between 5 and 18 carbon atoms in the part of the ring, such as, but not limited to, phenyl, naphthyl, diphenyl, indenyl, phenanthryl, fluorenyl or anthracyl Preferably the aryl group has 5 to 7 carbon atoms and more preferably the aryl group is a phenyl. The aryl groups can optionally be substituted in any of their positions by one or more substitutes or by two substitutes forming an aryl condensed cycle and are independently selected from among such as $CF_3$, $C_1$-$C_6$ alkyl, S—$C_1$-$C_6$ alkyl, halogen, CN, O—$C_1$-$C_6$ Alkyl, $NO_2$, COO—$C_1$-$C_6$ alkyl, NHCO—$C_1$-$C_6$ alkyl, $NH_2$ and NH—$C_1$-$C_6$ alkyl, and more preferably between $CF_3$, $C_1$-$C_6$ alkyl, halogen, CN and $NO_2$.

The term "heteroaryl" refers to an aryl, as defined above, which contains at least one distinct carbon atom, such as S, N, or O, forming part of the aromatic ring. The heteroaryl groups can optionally be substituted in any of their positions by one or more substituents or by two substituents forming a heteroaryl condensed cycle and are independently selected among such as $CF_3$, $C_1$-$C_6$ alkyl, S—$C_1$-$C_6$ alkyl, halogen, CN, O—$C_1$-$C_6$ alkyl, $NO_2$, COO—$C_1$-$C_6$ alkyl, NHCO—$C_1$-$C_6$ alkyl, $NH_2$ and NH—$C_1$-$C_6$ alkyl, and more preferably between $CF_3$, $C_1$-$C_6$ alkyl, halogen, CN and $NO_2$.

The term "alkyl" refers, in this invention, to saturated, linear or branched hydrocarbon chains, having from 1 to 10 carbon atoms, e.g. methyl, ethyl, n-propyl, i-propyl, n-butyl, tert-butyl, sec-butyl, n-pentyl, n-hexyl, etc. Preferably the alkyl group has between 1 and 6 carbon atoms and more the alkyl group has between 1 and 3 carbon atoms. Alkyl groups may optionally be replaced by one or more substitutes such as $CF_3$, $C_1$-$C_6$ alkyl, S—$C_1$-$C_6$ alkyl, halogen, CN, O—$C_1$-$C_6$ alkyl, $NO_2$, COO—$C_1$-$C_6$ alkyl, NHCO—$C_1$-$C_6$ alkyl, $NH_2$ and NH—$C_1$-$C_6$alkyl, and more preferably between $CF_3$, halogen, CN and $NO_2$.

"Halogen" in this invention means an atom of bromine, chlorine, iodine or fluorine, preferably bromine, chlorine or iodine.

In a preferred realization of the compounds of formula (II), $R_1$ to $R_5$ are selected independently of between H, $CF_3$, halogen, $C_1$-$C_6$ alkyl, CN, $NO_2$ or two of the radicals $R_1$ to $R_5$ form a cycle condensed to phenyl.

More preferably $R_5$ is H and even more preferably at least one of $R_1$, $R_2$, $R_3$ or $R_4$ is Cl, Br, I, methyl, $CF_3$, CN or $NO_2$, more preferably at least one of $R_1$, $R_2$, $R_3$ or $R_4$ is Cl, Br, I, $CF_3$, CN or $NO_2$.

More preferably $R_5$ is H and even more preferably two of the radicals $R_1$ to $R_4$ form a cycle condensed to phenyl, more preferably $R_1$ and $R_2$ form a cycle condensed to phenyl, even more preferably forming a naphthyl.

In another preferred performance, $R_1$, $R_2$, $R_3$, $R_4$ and $R_5$ are H.

In a more preferred realization the compound formula (I) or (II) is selected from among:
6-(benzylthio)-9H-purine (1)
6-((Naphthalene-1-ylmethyl)thio)-9H-purine (2)
6-((3-(cyanobenzyl)thio)-9H-purine (3)
6-((2-(trifluoromethyl)benzyl)thio)-9H-purine (4)
6-((4-chlorobenzyl)thio)-9H-purine (5)
6-((3-chlorobenzyl)oxy)-9H-purine (6)
6-((3-(trifluoromethyl)benzyl)thio)-9H-purine (7)
6-((3-chlorobenzyl)thio)-9H-purine (8)
6-((3-iodobenzyl)thio)-9H-purine (9)
6-((3-nitrobenzyl)thio)-9H-purine (10)
6-((3-bromobenzyl)thio)-9H-purine (11)
6-((4-bromobenzyl)thio)-9H-purine (12) and
6-((2-bromobenzyl)thio)-9H-purine (13)
6-((2-chlorobenzyl)thio)-9H-purine (14)
6-(3-methoxybenzyl)thio)-9H-purine (15)
Ethyl 2-((9H-purine-6-yl)thio)methyl)benzoate (16)
6-((4-nitrobenzyl)thio)-9H-purine (17)
6-((4-acetamidobenzyl)thio)-9H-purine (18)
6-((4-cyanobenzyl)thio)-9H-purine (19)
6-((benzyl)oxy)-9H-purine (20)
6-((4-bromobenzyl)oxy)-9H-purine (21)
6-(4-(trifluoromethyl)benzylthio)-9H-purine (22)
6-((4-(methylthio)benzyl)thio)-9H-purine (23).

Preferably the TDP-43 related disease is a neurological or neurodegenerative disease and can be selected primarily from amyotrophic lateral sclerosis, frontotemporal dementia and Alzheimer's disease, it can also be selected between chronic traumatic encephalopathy and age-associated cognitive impairment. Preferably the disease is selected between amyotrophic lateral sclerosis, frontotemporal dementia, Alzheimer's disease and age-associated cognitive impairment, even more preferably the disease is amyotrophic lateral sclerosis.

Another aspect of the invention concerns a compound, henceforth composed of the second aspect of the invention, which is selected from among:
6-((Naphthalene-1-ylmethyl)thio)-9H-purine (2)
6-((3-(cyanobenzyl)thio)-9H-purine (3)
6-((4-chlorobenzyl)thio)-9H-purine (5)
6-((3-chlorobenzyl)oxy)-9H-purine (6)
6-((3-(trifluoromethyl)benzyl)thio)-9H-purine (7)
6-((3-chlorobenzyl)thio)-9H-purine (8)
6-((3-iodobenzyl)thio)-9H-purine (9)
6-((3-nitrobenzyl)thio)-9H-purine (10) and
6-((2-bromobenzyl)thio)-9H-purine (13)
6-((2-chlorobenzyl)thio)-9H-purine (14)
Ethyl 2-((9H-purine-6-yl)thio)methyl)benzoate (16)
6-((4-acetamidobenzyl)thio)-9H-purine (18)
6-((4-cyanobenzyl)thio)-9H-purine (19)
6-((4-bromobenzyl)oxy)-9H-purine (21)
6-((4-(methylthio)benzyl)thio)-9H-purine (23).

Another aspect of the present invention relates to a pharmaceutical composition comprising at least one compound of the second aspect of the invention together with a pharmaceutically acceptable vehicle and may optionally comprise another active ingredient.

A further aspect of the present invention refers to the use of a compound of the second aspect of the invention for the manufacture of a medicament.

The compounds of the present invention represented by the formula (I), (II) or by the compounds of the second aspect of the invention, can include isomers, depending on the presence of multiple bonds (for example, Z, E), including optical isomers or enantiomers, depending on the presence of chiral centers. Individual isomers, enantiomers or diastereoisomers and mixtures thereof fall within the scope of the present invention, i.e., the term isomer also refers to any mixture of isomers, such as diastereomers, racemics, etc., including their optically active isomers or mixtures in different proportions thereof. Individual enantiomers or diastereoisomers, as well as their mixtures, can be separated using conventional techniques.

All compounds described in the invention can be in crystalline form as free compounds or as solvates. In this sense, the term "solvate", as used here, includes both pharmaceutically acceptable solvates, i.e., formula (I) compound solvates that may be used in the manufacture of a medicament, and pharmaceutically unacceptable solvates, which may be useful in the preparation of pharmaceutically acceptable solvates or salts. The nature of pharmaceutically acceptable solvent is not critical as long as it is pharmaceutically acceptable. In a particular application, the solvent is a hydrate. Solvates can be obtained by conventional solvation methods known to experts in the field.

For application in therapy, the compounds of formula (I), (II) or the compounds of the second aspect of the present invention, their salts, solvates or isomers, will be found, preferably, in a pharmaceutically acceptable or substantially pure form, that is to say, that it has a level of pharmaceutically acceptable purity excluding normal pharmaceutical additives such as thinners and carriers, and not including material considered toxic at normal dosage levels. The purity levels for the active ingredient are preferably above 50%, most preferably above 70%, and even more preferably above 90%. In a preferred realization, they are greater than 95% of compound formula (I), (II) or compounds of the second aspect of the present invention, or of its salts, solvates or isomers.

In another respect, the present invention refers to pharmaceutical compositions comprising at least one compound of the invention, or an isomer, a pharmaceutically acceptable salt or a derivative thereof, together with a pharmaceutically acceptable carrier, excipient or vehicle, for administration to a patient.

In a preferred formulation, the pharmaceutical composition also includes another active ingredient.

The pharmaceutically acceptable adjuvants and vehicles that may be used in such compositions are the adjuvants and vehicles known to those skilled in the art and commonly used in the development of therapeutic compositions.

Another aspect of the invention is a method of treatment of a neurological or neurodegenerative disease, which involves the administration to a patient of a therapeutically effective amount of a compound formula (I), preferably formula (II), or of a pharmaceutical composition comprising it, where neurological or neurodegenerative disease is a protein-related disease TDP-43 that can be selected primarily from amyotrophic lateral sclerosis, frontotemporal dementia, Alzheimer's disease, age-associated cognitive impairment, and chronic traumatic encephalopathy.

In the sense used in this description, the term "therapeutically effective quantity" refers to the quantity of the agent or compound capable of developing the therapeutic action determined by its pharmacological properties, calculated to produce the desired effect and, in general, will be determined, among other causes, by the characteristics of the compounds themselves, including age, the state of the patient, the severity of the alteration or disorder, and the route and frequency of administration.

The compounds described in the present invention, their salts or solvates, as well as the pharmaceutical compositions containing them may be used together with other drugs, or additional active ingredients, to provide a combination therapy. Such additional drugs may be part of the same pharmaceutical composition or, alternatively, may be provided in the form of a separate composition for simultaneous or non-simultaneous administration to the pharmaceutical composition comprising a compound of formula (I), preferably a compound of formula (II), or a salt or solvent thereof.

In another particular development, this therapeutic composition is prepared in the form of a solid form or aqueous suspension, in a pharmaceutically acceptable diluent. The therapeutic composition provided by this invention may be administered by any appropriate route of administration, for which such composition shall be formulated in the pharmaceutical form appropriate to the chosen route of administration. In a particular realization, the administration of the therapeutic composition provided by this invention is done orally, topically, rectally or parenterally (including subcutaneous, intraperitoneal, intradermal, intramuscular, intravenous, etc.).

In a preferred realization of the present invention, pharmaceutical compositions are suitable for oral administration, in solid or liquid form. Possible forms for oral administration are tablets, capsules, syrups or solutions and may contain conventional excipients known in the pharmaceutical field, such as aggregating agents (e.g. syrup, acacia, gelatine, sorbitol, tragacanth or polyvinyl pyrrolidone), fillers (e.g. lactose, sugar, corn starch, calcium phosphate, sorbitol or glycine), disintegrants (e.g. starch, polyvinyl pyrrolidone or microcrystalline cellulose) or a pharmaceutically acceptable surfactant such as sodium lauryl sulfate.

The compositions for oral administration can be prepared by the conventional methods of Galenic Pharmacy, as mixture and dispersion. The tablets can be coated following methods known in the pharmaceutical industry.

Pharmaceutical compositions can be adapted for parenteral administration, such as sterile solutions, suspensions, or freeze-dried products of the invention, using the appropriate dose. Suitable excipients, such as pH buffering agents or surfactants, may be used.

The above mentioned formulations can be prepared using conventional methods, such as those described in the Pharmacopoeias of different countries and in other reference texts.

The administration of the compounds or compositions of this invention can be performed by any appropriate method, such as intravenous infusion and oral, intraperitoneal or intravenous routes. Oral administration is preferred for the convenience of patients and for the chronic nature of the diseases to be treated.

The amount of a compound administered from the present invention will depend on the relative efficacy of the compound chosen, the severity of the disease to be treated and the weight of the patient. However, the compounds of this invention will be administered one or more times a day, for example 1, 2, 3 or 4 times a day, with a total dose between 0.1 and 1000 mg/Kg/day. It is important to keep in mind that it may be necessary to introduce variations in the dose, depending on the age and condition of the patient, as well as modifications in the route of administration.

The compounds and compositions of the present invention may be used together with other drugs in combination therapies. Other drugs may be part of the same composition or of a different composition, for administration at the same time or at different times.

The use of the compounds of the invention is compatible with their use in protocols in which the compounds of the formula (I), or their mixtures are used by themselves or in combinations with other treatments or any medical procedure.

Throughout the description and claims the word "comprise" and its variants are not intended to exclude other technical characteristics, additives, components or steps. For experts in the field, other objects, advantages and characteristics of the invention will be derived partly from the description and partly from the practice of the invention. The following examples and figures are provided by way of illustration, and are not intended to be limitative of the present invention.

EXAMPLES

Figure 1:
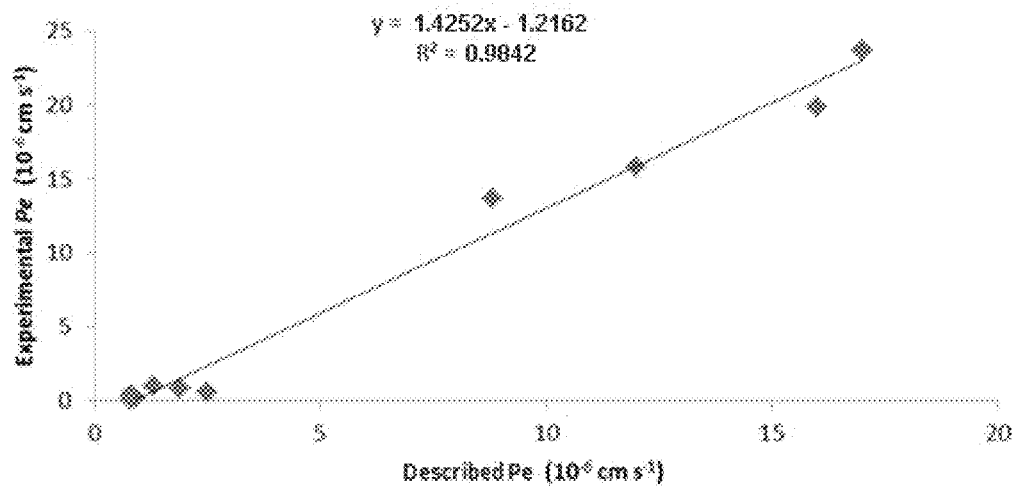
FIG. 1. Shows the linear correlation between the described permeability and the experimental permeability of 10 commercial compounds using the PAMPA methodology.

There follow illustrations of the invention by means of assays made by the inventors, which show the effectiveness of the product of the invention.

Example 1: Synthesis of the New Compounds of the Invention

Compound 1: 6-(benzylthio)-9H-purine

This compound is described in Pathak A. K. et al, *Journal of Medicinal Chemistry*, 2004, 47(1): 273-276.

Compound 2: 6-((Naphthalene-1-ylmethyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. Add 1-(chloromethyl)naphthalene (311.4 mg, 1.76 mmol) and stir overnight at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. Product 2 is thus obtained in the form of a white solid (218.0 mg, 42%). $^1$H-NMR (500 MHz, DMSO-$d_6$): δ 13.55 (s, 1H), 8.81 (s, 1H), 8.42 (s, 1H), 8.19 (dd, J=8.3, 1.4 Hz, 1H), 7.96 (dd, J=7.9, 1.5 Hz, 1H), 7.87 (d, J=8.1 Hz, 1H), 7.72 (dd, J=7.1, 1.3 Hz, 1H), 7.63-7.52 (m, 2H), 7.45 (dd, J=8.2, 7.0 Hz, 1H), 5.16 (s, 2H). $^{13}$C-NMR (125 MHz, DMSO-$d_6$): δ 158.2 (1C), 151.2 (1C), 149.4 (1C), 143.0 (1C), 133.5 (1C), 133.0 (1C), 131.1 (1C), 130.1 (1C), 128.7 (1C), 128.2 (1C), 127.7 (1C), 126.4 (1C), 126.0 (1C), 125.5 (1C), 123.7 (1C), 29.5 (1C), 125.5 (1C), 123.7 (1C), 29.5 (1C), 133.0 (1C), 128.2 (1C), 127.7 (1C), 126.4 (1C), 126.0 (1C), 125.5 (1C), 123.7 (1C), 29.5 (1C). HPLC: Purity>99%, r.t.=4.33 min. MS (ES): m/z 293 [M+1]. Melting point 221-222° C. Elemental analysis ($C_{16}H_{12}N_4S$) Calculated: C, 65.73%; H, 4.14%; N, 19.16%; S, 10.97%. Found: C, 65.41%; H, 4.07%; N, 19.11%; S, 10.99%.

Compound 3: 6-((3-(cyanobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. Add 3-(bromomethyl)benzonitrile (345.6 mg, 1.76 mmol) and stir overnight at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. It is not necessary to purify by means of a chromatographic column. In this way, product 3 is obtained in the form of a white solid (438.7 mg, 93%). $^1$H-NMR (300 MHz, DMSO-$d_6$): δ 13.57 (s, 1H), 8.74 (s, 1H), 8.46 (s, 1H), 7.93 (t, J=1.7 Hz, 1H), 7.85-7.79 (m, 1H), 7.71 (dt, J=7.8, 1.4 Hz, 1H), 7.52 (t, J=7.8 Hz, 1H), 4.70 (s, 2H). $^{13}$C-NMR (75 MHz, DMSO-$d_6$): δ 156.9 (1C), 151.4 (1C), 150.2 (1C), 143.5 (1C), 140.1 (1C), 134.0 (1C), 132.4 (1C), 130.9 (1C), 129.7 (2C), 118.6 (1C), 111.3 (1C), 30.7 (1C). MS (ES): m/z 268 [M+1]. Melting point 189-191° C. Elemental analysis ($C_{13}H_9N_5S$) Calculated: C, 58.41%; H, 3.39%; N, 26.20%; S, 12.00%. Found: C, 58.46%; H, 3.47%; N, 26.03%; S, 11.84%.

Compound 4: 6-((2-(trifluoromethyl)benzyl)thio)-9H-purine

This compound is described in Kamper C. et al., *Mol Diversity*, 2012, 16(3):541-551.

Compound 5: 6-((4-chlorobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. 4-chlorobenzene bromide (362.3 mg, 1.76 mmol) is added and agitated overnight at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. In this way, the product 5 is obtained in the form of a white solid (387.2 mg, 79%). $^1$H-NMR (300 MHz, DMSO-$d_6$): δ 13.55 (s, 1H), 8.73 (s, 1H), 8.45 (s, 1H), 7.55-7.43 (m, 2H), 7.42-7.29 (m, 2H), 4.65 (s, 2H). $^{13}$C-NMR (75 MHz, DMSO-$d_6$): δ 157.8 (1C), 151.4 (1C), 149.4 (1C), 143.2 (1C), 137.2 (1C), 131.7 (1C), 130.8 (2C), 130.0 (1C), 128.4 (2C), 30.8 (1C). MS (ES): m/z 279 [M+3], 277 [M+1]. Melting point 198-200° C. Elemental analysis ($C_{12}H_9ClN_4S$) Calculated: C, 52.08%; H, 3.28%; N, 20.24%; S, 11.59%. Found: C, 52.19%; H, 3.28%; N, 20.27%; S, 11.59%.

Compound 6: 6-((3-chlorobenzyl)oxy)-9H-purine

Dissolve 3-chlorobenzyl alcohol (2766.2 mg, 19.40 mmol) in NaOH (155.2 mg, 3.88 mmol) and heat until NaOH is dissolved. Cool the solution, add 6-chloro-9H-purine (300.0 mg, 1.94 mmol) and heat to 100° C. for 1 day. $Et_2O$ (120 mL) is added and extracted twice with an aqueous solution of NaOH 1% (70 mL). The aqueous phases are joined, washed with toluene and, after eliminating toluene, neutralised with 37% HCl up to pH 6-8. The solution is cooled in an ice bath and the precipitate obtained is collected by filtration. The crude compound is purified by chromatographic column using $CH_2Cl_2$/MeOH (10:1) as eluent. In this way, the product 6 is obtained in the form of a white solid (153.7 mg, 30%). $^1$H-NMR (300 MHz, DMSO-$d_6$): δ 13.48 (s, 1H), 8.52 (s, 1H), 8.41 (s, 1H), 7.60 (s, 1H), 7.53-7.45 (m, 1H), 7.45-7.38 (m, 2H), 5.62 (s, 2H). $^{13}$C-NMR (75 MHz, DMSO-$d_6$): δ 158.4 (1C), 155.4 (1C), 151.2 (1C), 143.0 (1C), 139.0 (1C), 133.1 (1C), 130.4 (1C), 128.0 (1C), 127.9 (1C), 126.7 (1C), 118.0 (1C), 66.7 (1C). Melting point 197-199° C. Elemental analysis ($C_{12}H_9ClN_4O$) Calculated: C, 55.29%; H, 3.48%; N, 21.49%. Found: C, 55.12%; H, 3.51%; N, 21.34%.

Compound 7: 6-((3-(trifluoromethyl)benzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. 3-(trifluoromethyl)benzyl bromide (421.4 mg, 1.76 mmol) is added and agitated overnight at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. This produces product 7 in the form of a white solid (283.3 mg, 52%). $^1$H-NMR (300 MHz, DMSO-$d_6$): δ 13.57 (s, 1H), 8.74 (s, 1H), 8.46 (s, 1H), 7.86 (s, 1H), 7.79 (d, J=7.3 Hz, 1H), 7.65-7.49 (m, 2H), 4.74 (s, 2H). $^{13}$C-NMR (75 MHz, DMSO-$d_6$): δ 157.2 (1C), 151.4 (1C), 150.2 (1C), 143.5 (1C), 139.8 (1C), 133.1 (1C), 129.5 (2C), 129.1 (c, J=31.4 Hz, 1C), 125.5 (c, J=3.9 Hz, 1C), 124.1 (m, 1C), 123.8 (c, J=3.9 Hz, 1C), 30.9 (1C). MS (ES): m/z 311 [M+1]. Melting point 180-182° C. Elemental analysis ($C_{13}H_9F_3N_4S$) Calculated: C, 50.32%; H, 2.92%; N, 18.06%; S, 10.33%. Found: C, 50.49%; H, 3.03%; N, 18.03%; S, 10.32%.

Compound 8: 6-((3-Chlorobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. 3-chlorobenzyl bromide (362.3 mg, 1.76 mmol) is added and agitated overnight at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. In this way the product 8 is obtained in the form of a white solid (233.1 mg, 48%). $^1$H-NMR (300 MHz, DMSO-$d_6$): δ 13.56 (s, 1H), 8.74 (s, 1H), 8.46 (s, 1H), 7.54 (t, J=2.0 Hz, 1H), 7.47-7.40 (m, 1H), 7.39-7.27 (m, 2H), 4.66 (s, 2H). $^{13}$C-NMR (75 MHz, DMSO-$d_6$): δ 157.3 (1C), 151.4 (1C), 149.5 (1C), 143.4 (1C), 140.8 (1C), 132.9 (1C), 130.3 (2C), 128.8 (1C), 127.7 (1C), 127.1 (1C), 30.9 (1C). MS (ES): m/z 279 [M+3], 277 [M+1]. Melting point 167-169° C. Elemental analysis ($C_{12}H_9ClN_4S$) Calculated: C, 52.08%; H, 3.28%; N, 20.24%; S, 11.59%. Found: C, 51.98%; H, 3.28%; N, 20.21%; S, 11.58%.

Compound 9: 6-((3-Iodobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. Add 3-iodobenzyl bromide (523.5 mg, 1.76 mmol) and stir for 4 hours at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. It is not necessary to purify by means of a chromatographic column. In this way, the product 9 is obtained in the form of a pale yellow solid (379.6 mg, 58%). $^1$H-NMR (300 MHz, DMSO-$d_6$): δ 13.56 (s, 1H), 8.74 (s, 1H), 8.46 (s, 1H), 7.85 (t, J=1.8 Hz, 1H), 7.60 (dt, J=7.6, 1.4 Hz, 1H), 7.48 (dt, J=7.6, 1.4 Hz, 1H), 7.11 (t, J=7.8 Hz, 1H), 4.61 (s, 2H). $^{13}$C-NMR (75 MHz, DMSO-$d_6$): δ 157.3 (1C), 151.4 (1C), 149.8 (1C), 143.4 (1C), 140.8 (1C), 137.4 (1C), 135.8 (1C), 130.6 (1C), 129.8 (1C), 128.4 (1C), 94.7 (1C), 30.7 (1C). Melting point 185-187° C. Elemental analysis ($C_{12}H_9IN_4S$) Calculated: C, 39.14%; H, 2.46%; N, 15.22%; S, 8.71%. Found: C, 39.26%; H, 2.53%; N, 15.05%; S, 8.58%.

Compound 10: 6-((3-nitrobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. 3-nitrobenzyl bromide (380.9 mg, 1.76 mmol) is added and agitated for 3 hours at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. It is not necessary to purify by means of a chromatographic column. In this way the product 10 is obtained in the form of a pale yellow solid (460.6 mg, 91%). $^1$H-NMR (300 MHz, DMSO-$d_6$): δ 13.58 (s, 1H), 8.74 (s, 1H), 8.47 (s, 1H), 8.36 (t, J=2.0 Hz, 1H), 8.09 (ddd, J=8.4, 2.3, 1.1 Hz, 1H), 7.94 (dt, J=7.8, 1.2 Hz, 1H), 7.60 (t, J=8.0 Hz, 1H), 4.79 (s, 2H). $^{13}$C-NMR (75 MHz, DMSO-$d_6$): δ 156.8 (1C), 151.4 (1C), 150.2 (1C), 147.7 (1C), 143.6 (1C), 140.9 (1C), 135.7 (1C), 129.9 (2C), 123.6 (1C), 122.0 (1C), 30.6 (1C). Melting point 193-195° C. Elemental analysis ($C_{12}H_9N_5O_2S$) Calculated: C, 50.17%; H, 3.16%; N, 24.38%; S, 11.16%. Found: C, 50.07%; H, 2.76%; N, 24.15%; S, 11.05%.

Compound 11: 6-((3-bromobenzyl)thio)-9H-purine

This compound is described in Kamper C. et al., *Mol Diversity*, 2012, 16(3):541-551.

Compound 12: 6-((4-bromobenzyl)thio)-9H-purine

This compound is described in Kamper C. et al., *Mol Diversity*, 2012, 16(3):541-551.

Compound 13: 6-((2-bromobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. 2-bromobenzyl bromide (440.6 mg, 1.76 mmol) is added and agitated for 4 hours at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. It is not necessary to purify by means of a chromatographic column. In this way the product 13 is obtained in the form of a white solid (462.3 mg, 82%). $^1$H-NMR (300 MHz, DMSO-$d_6$): δ 13.58 (s, 1H), 8.76 (s, 1H), 8.45 (s, 1H), 7.66 (dt, J=7.9, 1.8 Hz, 2H), 7.33 (td, J=7.5, 1.4 Hz, 1H), 7.22 (td, J=7.6, 1.8 Hz, 1H), 4.74 (s, 2H). $^{13}$C-NMR (75 MHz, DMSO-$d_6$): δ 157.7 (1C), 151.5 (1C), 149.4 (1C), 143.2 (1C), 136.8 (1C), 132.8 (1C), 131.5 (1C), 130.1 (1C), 129.6 (1C), 128.0 (1C), 124.2 (1C), 32.4 (1C). Melting point 209-211° C. Elemental analysis ($C_{12}H_9BrN_4S$) Calculated: C, 44.87%; H, 2.82%; N, 17.44%; S, 9.98%. Found: C, 44.96%; H, 2.83%; N, 17.43%; S, 9.97%.

Compound 14: 6-((2-Chlorobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. 2-chlorobenzyl bromide (362.3 mg, 1.76 mmol) is added and agitated overnight at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. In this way the compound 14 is obtained in the form of a white solid (235.5 mg, 48%). $^1$H-NMR (300 MHz, DMSO-$d_6$): δ 13.56 (s, 1H), 8.76 (s, 1H), 8.46 (s, 1H), 7.66 (dd, J=6.4 Hz, 3.0 Hz, 1H), 7.49 (dd, J=6.8, 2.5 Hz, 1H), 7.37-7.23 (m, 2H), 4.75 (s, 2H). $^{13}$C-NMR (75 MHz, DMSO-$d_6$): δ 157.6 (1C), 151.4 (1C), 149.4 (1C), 143.3 (1C), 135.1 (1C), 133.4 (1C), 131.4 (1C), 130.5 (1C), 129.5 (1C), 129.3 (1C), 127.4 (1C), 29.7 (1C). MS (ES): m/z 279 [M+3], 277 [M+1]. Melting point 200-202° C. Elemental analysis ($C_{12}H_9ClN_4S$) Calculated: C, 52.08%; H, 3.28%; N, 20.24%; S, 11.59%. Found: C, 52.12%; H, 3.33%; N, 20.08%; S, 11.38%.

Compound 15: 6-((3-methoxybenzyl)thio)-9H-purine

This compound is described in Patthack A K. et al., *J Med Chem*, 2004, 47(1):273-276.

Compound 16: Ethyl 2-(((9H-Purine-6-yl)thio)methyl)benzoate 6-mercaptopurine monohydrate (48.7 mg, 0.29 mmol) and $K_2CO_3$ (39.5 mg, 0.29 mmol) are dissolved in DMF (4 mL). Keep the reaction mixture in agitation for 1 h at room temperature. Add ethyl 2-(chloromethyl)benzoate (56.8 mg, 0.29 mmol) and stir overnight at room temperature. The solvent is evaporated at reduced pressure and AcOEt (50 mL) is added. The organic phase is washed with distilled water (3×50 mL) adding a little NaCl. It is dried on anhydrous $Mg_2SO_4$, filtered and concentrated to dryness. Crude oil is purified by recrystallization in EtOH. In this way the compound 16 is obtained in the form of a white solid (22.0 mg, 24%). $^1$H-NMR (500 MHz, DMSO-$d_6$): δ 13.51 (s, 1H), 8.73 (s, 1H), 8.41 (s, 1H), 7.87 (dd, J=7.8, 1.4 Hz, 1H), 7.69 (dd, J=7.8, 1.2 Hz, 1H), 7.52 (td, J=7.5, 1.5 Hz, 1H), 7.39 (td, J=7.6, 1.3 Hz, 1H), 4.96 (s, 2H), 4.34 (q, J=7.1 Hz, 2H), 1.33 (t, J=7.1 Hz, 3H). $^{13}$C-NMR (125 MHz, DMSO-$d_6$): δ 166.6 (1C), 158.3 (1C), 151.3 (1C), 149.3 (1C), 143.0 (1C), 139.4 (1C), 132.3 (1C), 131.4 (1C), 130.4 (1C), 130.0 (1C), 129.5 (1C), 127.6 (1C), 61.0 (1C), 30.0 (1C), 14.0 (1C). Melting point 145-147° C. Elemental analysis ($C_{15}H_{14}N_4O_2S$) Calculated: C, 57.31%; H, 4.49%; N, 17.82%; S, 10.20%. Found: C, 56.91%; H, 4.72%; N, 17.19%; S, 9.84%.

Composite 17: 6-((4-nitrobenzyl)thio)-9H-purine

This compound is described in Tromp R. et al., *J Med Chem*, 2004, 47(22):5441-5450.

Compound 18: 6-((4-Acetamidobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. Add 4-acetamidobenzyl chloride (323.8 mg, 1.76 mmol) and agitate for 3 h 30 min at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. In this way, compound 18 is obtained in the form of a pale yellow solid (207.2 mg, 39%). $^1$H-NMR (300 MHz, DMSO-$d_6$): δ 13.53 (s, 1H), 9.93 (s, 1H), 8.73 (s, 1H), 8.44 (s, 1H), 7.51 (d, J=8.5 Hz, 2H), 7.37 (d, J=8.5 Hz, 2H), 4.59 (s, 2H), 2.01 (s, 3H). $^{13}$C-NMR (75 MHz, DMSO-$d_6$): δ 168.2 (1C), 158.4 (1C), 151.4 (1C), 149.3 (1C), 143.0 (1C), 138.4 (1C), 132.1 (1C), 130.1 (1C) 129.4 (2C), 119.0 (2C), 31.4 (1C), 24.0 (1C). HPLC: Purity>99%, r.t.=5.25 min. MS (ES): m/z 300 [M+1]. Melting point 223-225° C. Elemental analysis ($C_{14}H_{13}N_5OS$) Calculated: C, 56.17%; H, 4.38%; N, 23.40%; S, 10.71%. Found: C, 55.54%; H, 4.51%; N, 22.67%; S, 10.27%.

Compound 19: 6-((4-Cyanobenzyl)thio)-9H-purine 6-mercaptopurine monohydrate (300.0 mg, 1.76 mmol) and $K_2CO_3$ (243.7 mg, 1.76 mmol) are dissolved in DMF (25 mL). Keep the reaction mixture in agitation for 1 h at room temperature. Add 4-cyanobenzyl bromide (345.6 mg, 1.76 mmol) and agitate for 2 hours at room temperature. The solvent is evaporated at reduced pressure and AcOEt (100 mL) is added. The organic phase is washed with distilled water (3×100 mL) adding a little NaCl. It is dried on anhydrous $Mg_2SO_4$, filtered and concentrated to dryness. The crude compound is purified by chromatographic column using $CH_2Cl_2$/MeOH (10:1) as eluent. In this way the compound 19 is obtained in the form of a white solid (358.7 mg, 76%). $^1$H-NMR (300 MHz, DMSO-$d_6$): δ 13.57 (s, 1H), 8.73 (s, 1H), 8.46 (s, 1H), 7.77 (d, J=7.7 Hz, 2H), 7.66 (d, J=8.0 Hz, 2H), 4.72 (s, 2H). $^{13}$C-NMR (75 MHz, DMSO-$d_6$): δ 157.2 (1C), 151.4 (1C), 149.9 (1C), 144.3 (1C), 143.5 (1C), 132.4 (2C), 130.0 (2C), 129.6 (1C), 118.8 (1C), 109.8 (1C), 31.1 (1C). Melting point 228-230° C. Elemental analysis ($C_{13}H_9N_5S$) Calculated: C, 58.41%; H, 3.39%; N, 26.20%; S, 11.99%. Found: C, 58.30%; H, 3.43%; N, 26.10%; S, 11.87%.

Compound 20: 6-((benzyl)oxy)-9H-purine

This compound is described in Wanner M J. et al., *J Med Chem*, 2004, 47(27):6875-6883.

Compound 21: 6-((4-Bromobenzyl)oxy)-9H-purine

Dissolve 4-bromobenzyl alcohol (1815.1 mg, 9.70 mmol) and NaOH (155.2 mg, 3.88 mmol) in a little MeOH (25 mL). The reaction mixture is kept in agitation until the NaOH is dissolved. Add 6-chloro-9H-purine (300.0 mg, 1.94 mmol) and heat to (90° C.) for 2 h. The solvent is evaporated at reduced pressure and AcOEt (50 mL) is added. The organic phase is washed with distilled water (3×50 mL) adding a little NaCl. It is then dried on anhydrous $Mg_2SO_4$, filtered and concentrated to dryness. The crude compound is purified by chromatographic column using $CH_2Cl_2$/MeOH (10:1) as eluent. In this way the compound 21 is obtained in the form of beige solid (107.2 mg, 18%). $^1$H-NMR (300 MHz, DMSO-$d_6$): δ 13.48 (s, 1H), 8.51 (s, 1H), 8.40 (s, 1H), 7.61 (d, J=8.4 Hz, 2H), 7.48 (d, J=8.4 Hz, 2H), 5.59 (s, 2H).

$^{13}$C-NMR (75 MHz, DMSO-d$_6$): δ 158.5 (1C), 155.3 (1C), 151.2 (1C), 143.0 (1C), 136.0 (1C), 131.4 (2C), 130.4 (2C), 121.3 (1C), 118.1 (1C), 66.8 (1C). Melting point ° C. Elemental analysis (C$_{12}$H$_9$BrN$_4$O) Calculated: C, 47.24%; H, 2.97%; N, 18.36%. Found: C, 47.06%; H, 2.98%; N, 18.31%.

Compound 22:
6-(4-(trifluoromethyl)benzylthio)-9H-purine

This compound is described in Kamper C. et al., *Mol Diver*, 2012, 16(3):541-551.

Compound 23:
6-((4-(Methylthio)benzyl)thio)-9H-purine 6-mercaptopurine monohydrate (300.0 mg, 1.76 mmol) and K$_2$CO$_3$ (243.7 mg, 1.76 mmol) are dissolved in DMF (25 mL). Keep the reaction mixture in agitation for 1 h at room temperature. Add 4-(methylthio)benzyl bromide (382.8 mg, 1.76 mmol) and stir overnight at room temperature. The solvent is evaporated at reduced pressure and AcOEt (100 mL) is added. The organic phase is washed with distilled water (3×100 mL) adding a little NaCl. It is dried on anhydrous Mg$_2$SO$_4$, filtered and concentrated to dryness. The crude compound is purified by chromatographic column using CH$_2$Cl$_2$/MeOH (10:1) as eluent. In this way, compound 24 is obtained in the form of a white solid (158.0 mg, 31%). $^1$H-NMR (300 MHz, DMSO-d$_6$): δ 13.53 (s, 1H), 8.73 (s, 1H), 8.44 (s, 1H), 7.40 (d, J=8.2 Hz, 2H), 7.20 (d, J=8.3 Hz, 2H), 4.61 (s, 2H), 2.44 (s, 3H). $^{13}$C-NMR (125 MHz, DMSO-d$_6$): δ 158.2 (1C), 151.4 (1C), 149.3 (1C), 143.0 (1C), 136.9 (1C), 134.5 (1C), 130.1 (1C), 129.6 (2C), 126.0 (2C), 31.2 (1C), 14.7 (1C). MS (ES): m/z 289 [M+1]. Melting point 203-205° C. Elemental analysis (C$_{13}$H$_{12}$N$_4$S2) Calculated: C, 54.14%; H, 4.19%; N, 19.43%; S, 22.24%. Found: C, 53.96%; H, 4.15%; N, 19.34%; S, 22.19%.

Example 2: CDC7 Inhibition Measurement
(ADP-Glo Technology)™

The method used is a non-radioactive enzyme inhibition assay using human recombinant CDC7. It is based on luminometric quantification of inhibition using the ADP-Glo™ Kinase Kit. In this test the luminescent signal correlates positively with the amount of adenosine diphosphate (ADP) and the activity of the kinase. All compounds were evaluated at a fixed concentration of 10 μM. For compounds with an inhibition percentage greater than 50%, a dose-response study is carried out to determine their CI$_{50}$ value (concentration of a compound capable of inhibiting CDC7 function by 50%).

CDC7 enzyme inhibition studies were conducted using the promega kit: ADP-Glo™ Kinase Assay+CDC7/DBF4 Kinase Enzyme System (Catalogue No. V5089). ATP and other reagents were purchased in Sigma-Aldrich (St. Louis, Mo.). The trials were performed in a buffer solution using 96-well plates. The compound to be tested (5 μL, 40 μM dissolved in DMSO 4%) was added to each well followed by the enzyme (5 μL, 25 ng/well), ATP (5 μL, final concentration in well 10 μM) and PDKtidE (5 μL, 4 μg/well). It was then incubated for 60 minutes at room temperature and the reagent ADP-Glo™ (20 μL) was added and incubated again for 40 min at room temperature. After incubation, the kinase detection agent (40 μL) was added and incubated for 30 min at room temperature. Finally, the luminescence (integration time of 0.5-1 sec) was measured using a POLARstar Optima multimode reader polarimeter. Inhibition activities were calculated as a function of maximum activity, measured in the absence of inhibitor. The inhibition values determined for prepared compounds are listed in Table 1.

Example 3: CDC7 Inhibition Measurement
(LanthaScreen Technology)

The LanthaScreen Eu kinases inhibition assay uses an Alexa marker Fluor™ that binds to a kinase and is detected by the addition of an Eu-marked antibody. The binding of the marker and the antibody to the kinase results in a high degree of FRET, while the displacement of the marker by an inhibitor results in a loss of FRET. Unlike many other kinase activity tests, this is a simple mix and read test, with no developmental stages. This test method has been developed by Life Technologies and identifies competitive ATP kinase inhibitors, making them suitable for the detection of any compound that binds to the ATP site.

The compounds are evaluated at 1% DMSO (final) in the well. A mixture of human recombinant CDC7/DBF4 (0.5 nM), Eu-antiGST antibody (2 nM) and AlexaFluor marker (1 nM) has been used in a buffer of 50 mM HEPES pH 7.5, 0.01% BRIJ-35, 10 mM MgCl2, 1 mM EGTA in white plates of 348 wells, low volume, coded (Greiner cat. #784207), 160 nL (100×100% DMSO compound), 3.84 μL (buffer with CDC7/DBF4), 8.0 μL (antibody), 4.0 μL (marker) are added. Agitate 30 s and incubate at room temperature for 60 min. Then measure the fluorescence in the plate reader and analyze the data (Table 1).

TABLE 1

Inhibition values in CDC7 of the compounds of formula (II):

(II)

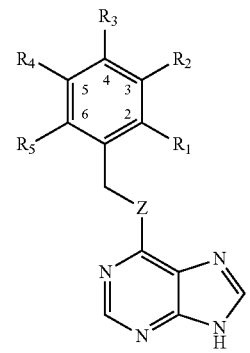

| Comp. | R$_1$ to R$_5$ | Z | CDC7 ADP-Glo ™ CI$_{50}$ (μM) | CDC7 Lantha ™ CI$_{50}$ (μM) |
|---|---|---|---|---|
| 1 | H | S | 6.74 ± 0.35 | 0.125 |
| 2 | 2.3-[(CH)$_4$] | S | 11.22 ± 0.84 | 0.347 |
| 3 | 3-CN | S | 8.38 ± 0.27 | 0.335 |
| 4 | 2-CF$_3$ | S | 9.73 ± 1.03 | 0.245 |
| 5 | 4-Cl | S | 8.46 ± 1.05 | 0.184 |
| 6 | 3-Cl | O | 8.98 ± 0.21 | 0.194 |
| 7 | 3-CF$_3$ | S | 6.90 ± 0.83 | 0.320 |
| 8 | 3-Cl | S | 5.21 ± 0.38 | 0.172 |
| 9 | 3-I | S | 3.34 ± 0.27 | 0.086 |
| 10 | 3-NO$_2$ | S | 6.54 ± 0.32 | 0.189 |
| 11 | 3-Br | S | 5.29 ± 0.71 | 0.138 |
| 12 | 4-Br | S | 9.14 ± 0.79 | 0.438 |
| 13 | 2-Br | S | 6.24 ± 0.99 | 0.275 |
| 14 | 2-Cl | S | | 0.092 |
| 15 | 3-OMe | S | | 0.239 |
| 16 | 2-CO2Et | S | | 2.790 |
| 17 | 4-NO2 | S | | 0.127 |

TABLE 1-continued

Inhibition values in CDC7 of the compounds of formula (II):

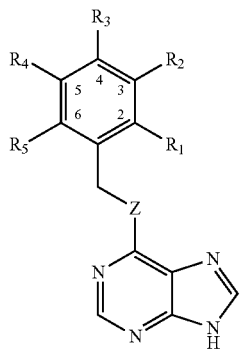

| Comp. | R₁ to R₅ | Z | CDC7 ADP-Glo™ CI₅₀ (μM) | CDC7 Lantha™ CI₅₀ (μM) |
|---|---|---|---|---|
| 18 | 4-NHCOMe | S | | 0.474 |
| 19 | 4-CN | S | | 0.288 |
| 20 | H | O | | 0.167 |
| 21 | 4-Br | O | | 0.909 |
| 22 | 4-CF3 | S | | 0.367 |
| 23 | 4-SCH3 | S | | 0.146 |

Example 3: Prediction of the Blood-Brain Barrier Permeation

An essential requirement for drugs for the treatment of neurodegenerative diseases is the ability to cross the blood-brain barrier (BBB), as otherwise they could not act on the target of interest. Therefore, for compounds that are not permeable or located in the area of uncertainty, it may be necessary to properly convey a pharmaceutical formulation through methods known to an expert in the field, such as encapsulation. This capability can be predicted in vitro using a method known by the acronym PAMPA (Parallel Artificial Membrane Permeability Assay) described by Di et al (Di, L.; Kerns, E. H.; Fan, K.; McConnell, O. J.; Carter, G. T. *Eur. J. Med. Chem.* 2003, 38 (3), 223-232) and which has subsequently been fine-tuned in our research group. This method allows predicting the effective permeability through artificial membranes by means of a passive diffusion process.

First of all, it is necessary to validate the method, for which 10 commercial compounds are used whose penetration capacity in the central nervous system (CNS) is known and which are to be specified below, obtaining in this case a good linear correlation between the experimental permeability values (Pe) and those described (FIG. 1). This correlation line obtained following the pattern described in the bibliography allows establishing the limits to predict whether or not a compound can cross the blood-brain barrier. Thus, a compound is considered BBB permeable (SNC+) if it has a permeability $>4.48 \times 10^{-6}$ cm·s$^{-1}$.

For the procedure, between 3-5 mg of caffeine, desipramine, enoxacin, hydrocortisone, ofloxacin, piroxicam and testosterone, 12 mg of promazine and 25 mg of atenolol and verapamil were taken and dissolved in EtOH (1000 μL). 100 μL of these solutions were taken and EtOH (1400 μL) and phosphate buffer (PBS) pH=7.4 (3500 μL) were added in order to achieve a final EtOH concentration of 30% v/v in solution. Finally, the dissolutions were filtered.

On the other hand, a PBS/EtOH solution (70:30) was added to each well of the acceptance plate (180 μL). The donor plate was impregnated with a porcine brain lipid solution (4 μL) dissolved in dodecane (20 mg mL$^{-1}$). After 5 min, dissolution of each compound was added to this plate (180 μL).

Of the compounds 1 to 10 evaluated, 1-2 mg were taken and dissolved in EtOH (1500 μL) and phosphate buffer (PBS) pH=7.4 (3500 μL), filtered and added to the donor plate. With these solutions, the wavelengths at which the compounds absorb are determined and the initial absorbance levels at these wavelengths are measured using a UV absorbance reader. Each sample was analyzed from two to five wavelengths, in three wells and in two independent experiments.

The donor plate was then deposited on the acceptor forming a kind of "sandwich" and incubated for 2 hours and 30 minutes at 25° C. In this way, the compounds will pass from the donor plate to the acceptor plate through the porcine brain lipid by passive diffusion. After that time, the donor plate is carefully removed and the concentration and final absorbance of both commercial and synthesized compounds is determined. The results obtained are expressed as the mean of the measurements [standard deviation (SD)] of the different experiments carried out and are shown in table 2.

TABLE 2

Permeability values (Pe 10⁻⁶ cm s⁻¹) in the PAMPA-BHE experiment and prediction of central nervous system (CNS) penetration of formula (II) compounds as also described in Table 1:

| Comp. | R₁ to R₅ | Z | Pe (10⁻⁶ cm s⁻¹) | PAMPA prediction |
|---|---|---|---|---|
| 1 | H | S | 6.2 ± 1.1 | SNC+ |
| 2 | 2.3-[(CH)₄] | S | 13.2 ± 2.0 | SNC+ |
| 3 | 3-CN | S | 2.3 ± 0.2 | SNC+/− |
| 4 | 2-CF₃ | S | 17.5 ± 0.9 | SNC+ |
| 5 | 4-Cl | S | 12.2 ± 1.2 | SNC+ |
| 6 | 3-Cl | O | 7.2 ± 0.6 | SNC+ |
| 7 | 3-CF₃ | S | 16.3 ± 0.6 | SNC+ |
| 8 | 3-Cl | S | 15.1 ± 0.6 | SNC+ |
| 9 | 3-I | S | 13.8 ± 2.5 | SNC+ |
| 10 | 3-NO₂ | S | 3.9 ± 0.4 | SNC+/− |
| 12 | 4-Br | S | 11.5 ± 0.7 | SNC+ |
| 13 | 2-Br | S | 13.1 ± 0.1 | SNC+ |
| 14 | 2-Cl | 5 | 18.1 ± 1.2 | SNC+ |
| 15 | 3-OMe | S | 5.3 ± 0.8 | SNC+ |
| 16 | 2-CO2Et | S | 9.7 ± 1.4 | SNC+ |
| 17 | 4-NO2 | S | 5.5 ± 1.3 | SNC+ |
| 19 | 4-CN | S | 2 ± 0.7 | SNC+/− |
| 20 | H | O | 2.9 ± 0.9 | SNC+/− |
| 21 | 4-Br | O | 14 ± 1.4 | SNC+ |
| 22 | 4-CF3 | — | 13.5 ± 1.6 | SNC+ |
| 23 | 4-SCH3 | — | 17.8 ± 0.7 | SNC+ |

Figure 2:
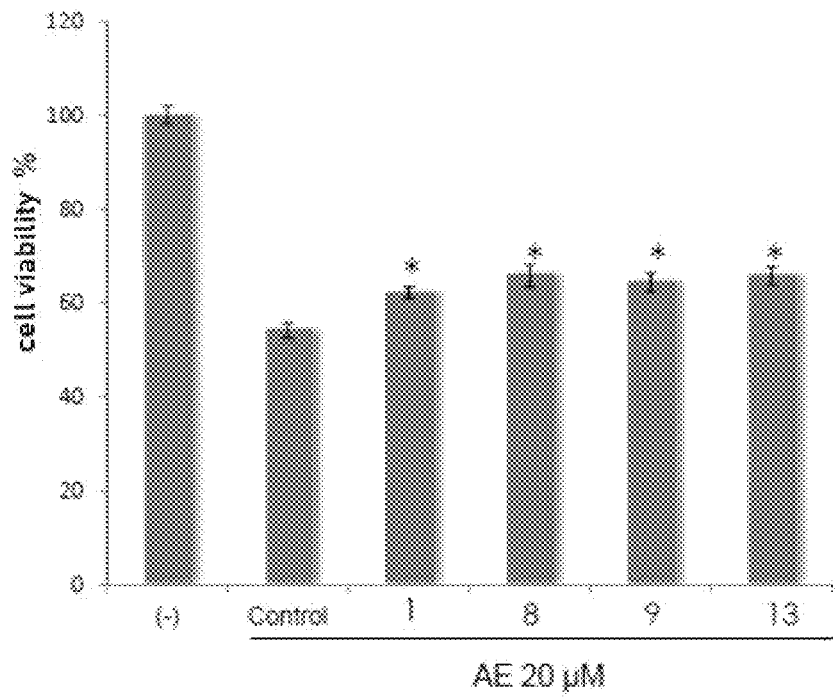
FIG. 2. Shows the neuroprotective effect of CDC7 inhibitors (compounds 1, 8, 9 and 13) on human SH-SY5Y neuroblastoma cells previously treated with ethacrynic acid (AE, 20 µM) for 12 hours in the presence or absence of inhibitors at 10 µM. The data represent the mean of four different±SEM experiments (*p<0.05).

Example 4: Neuroprotective Effect of CDC7 Inhibitors Against Ethacrynic Acid The human neuroblastoma cell line SH-SY5Y was cultured at 37° C. with 5% CO₂ in DMEN medium (Dulbecco's Modified Eagle Medium) enriched with L-glutamine (2 mM), 1% non-essential amino acids, 1% Penicillin/Estreptomycin and 10% fetal bobin serum. In the semiconfluence state, the cells were treated with CDC7 inhibitors (compounds 1 and 8) at different concentrations for 1.30 hours post-addition of the causative agent of TPD-43 phosphorylation; ethacrynic acid (20 NM) (Sigma). After 24 hours, cell viability was evaluated with MTT ([3-(4,5-dimethylthiazol2-yl)-2,5-diphenyltetrazolium bromide) following a described procedure (Denizot F, Lang R. *J Immunol Methods*. 1987; 89:271-7) and levels of western blot phosphorylated TDP-43 (FIG. 2).

Example 5: Effect of CDC 7 Inhibitors on Phosphorylation of TDP-43

Figure 3:
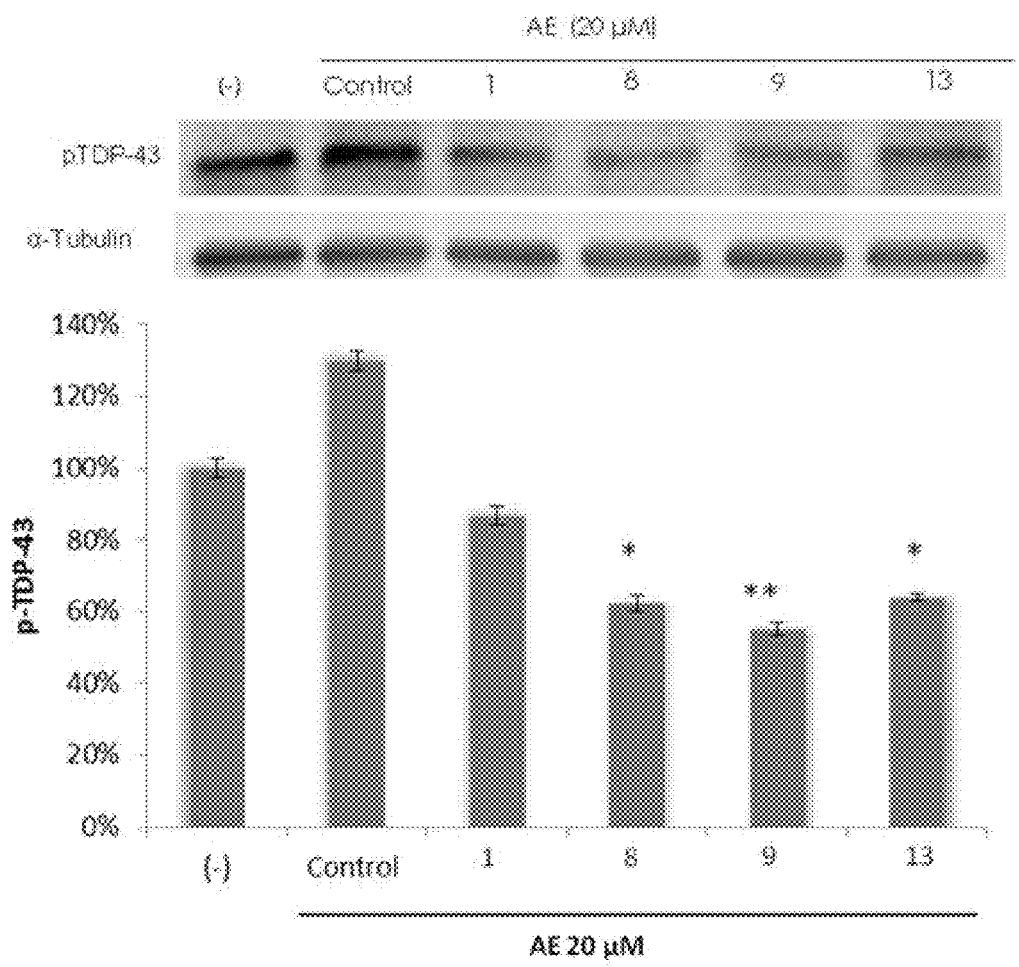
FIG. 3. Sample of the effect of CDC7 inhibitors (compounds 1, 8, 9 and 13) on TDP-43 phosphorylation. Quantification and representation of phosphorylated TDP-43 levels by western blot.

To evaluate the levels of TDP-43 phosphorylated in the presence of CDC7 inhibitors (compounds 1 and 8), the cells after 24 h of incubation with ethacrylic acid were washed with PBS and then cold lysed with lysis buffer (50 mM Tris pH 7.4, 150 mM NaCl, 50 mM NaF, 1% Nonidet P-40 and Protease and phosphatase inhibitors (Roche)). The collected cell extracts were centrifuged for 10 minutes at 4,000 rpm. Protein quantification was performed with the Pierce BCA protein assay kit (Thermo Scientific). 10 µg of protein were loaded into the polyacrylamide gel with SDS and subsequently transferred to a polyvinylidene fluoride (PVDF) membrane (Millipore). The membrane was blocked with 5% bovine serum albumin (Sigma), and incubated for 12 hours with the following primary antibody concentrations (anti-human phosphorus (S409/410)-TDP-43 (1:500) (22309-1AP, Proteintech); α-tubulin (1:1,000) (sc-23948, Santa Cruz Biotechnologies). Amplification of the signal was carried out with secondary antibodies conjugated to radish peroxidase, corresponding to the species used in the primary antibody (Bio-Rad). The density of the bands was quantified with the Image J program (National Institutes of Health, Bethesda, Md., USA). FIG. 3 shows that treatment of cells with CDC7 inhibitors (compounds of invention 1 and 8) made it possible to reduce phosphorylation of TDP-43.

The invention claimed is:

1. A method for the inhibition of CDC7 in the phosphorylation of TDP-43 for the treatment of pathologies related to the protein TDP-43, wherein the TDP-43 related disease is a neurological disease selected from amyotrophic lateral sclerosis, frontotemporal dementia, Alzheimer's disease, age-associated cognitive impairment, and chronic traumatic encephalopathy, the method comprising administering to a subject an effective amount of a compound according to formula (II):

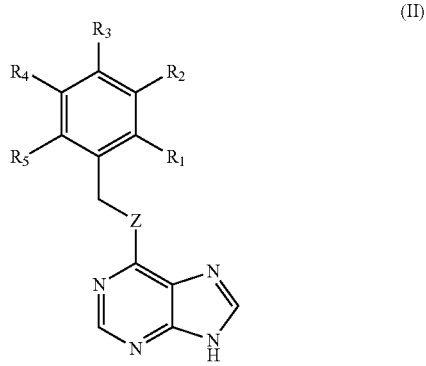

(II)

wherein $R_5$ is H and at least one of $R_1$, $R_2$, $R_3$ or $R_4$ is Cl, Br, I, methyl, $CF_3$, CN or $NO_2$; and Z is selected from O or S.

2. The method according to claim 1, wherein $R_5$ is H.

3. The method according to claim 1, wherein at least one of $R_1$, $R_2$, $R_3$ or $R_4$ is Cl, Br or I and $R_5$ is H.

4. The method according to claim 1, wherein at least one of $R_1$, $R_2$, $R_3$ or $R_4$ is methyl, $CF_3$, CN or $NO_2$ and $R_5$ is H.

5. The method according to claim 1, wherein two of the radicals $R_1$ to $R_4$ form a phenyl-condensed cycle and $R_5$ is H.

6. The method according to claim 1, wherein the compound is selected from:

6-((3-(cyanobenzyl)thio)-9H-purine, 6-((2-(trifluoromethyl)benzyl)thio)-9H-purine, 6-((4-chlorobenzyl)thio)-9H-purine, 6-((3-chlorobenzyl)oxy)-9H-purine, 6-((3-(trifluoromethyl)benzyl)thio)-9H-purine, 6-((3-chlorobenzyl)thio)-9H-purine, 6-((3-iodobenzyl)thio)-9H-purine, 6-((3-nitrobenzyl)thio)-9H-purine, 6-((3-bromobenzyl)thio)-9H-purine, 6-((4-bromobenzyl)thio)-9H-purine, 6-((2-bromobenzyl)thio)-9H-purine, 6-((2-chlorobenzyl)thio)-9H-purine, 6-((4-nitrobenzyl)thio)-9H-purine, 6-((4-cyanobenzyl)thio)-9H-purine, 6-((4-bromobenzyl)oxy)-9H-purine, and 6-(4-(trifluoromethyl)benzylthio)-9H-purine.

7. The method according to claim 1, wherein the disease is selected from amyotrophic lateral sclerosis, frontotemporal dementia and Alzheimer's disease.

8. A compound selected from:

6-((3-chlorobenzyl)oxy)-9H-purine, 6-((3-iodobenzyl)thio)-9H-purine, and 6-((4-bromobenzyl)oxy)-9H-purine.

9. A pharmaceutical composition comprising the compound of claim 8 and a pharmaceutically acceptable vehicle.

* * * * *